(12) United States Patent
Mercado

(10) Patent No.: US 10,736,700 B2
(45) Date of Patent: Aug. 11, 2020

(54) ERGONOMIC FOOT-OPERATED SYSTEM

(71) Applicant: Novartis AG, Basel (CH)

(72) Inventor: Fred Mercado, Laguna Hills, CA (US)

(73) Assignee: Alcon Inc., Rue Louis-d'affry, Fribourg (CH)

( * ) Notice: Subject to any disclaimer, the term of this patent is extended or adjusted under 35 U.S.C. 154(b) by 266 days.

(21) Appl. No.: 15/807,769

(22) Filed: Nov. 9, 2017

(65) Prior Publication Data

US 2018/0132948 A1    May 17, 2018

Related U.S. Application Data

(60) Provisional application No. 62/423,272, filed on Nov. 17, 2016.

(51) Int. Cl.

| | |
|---|---|
| *A61B 34/00* | (2016.01) |
| *A61B 34/30* | (2016.01) |
| *G01L 1/04* | (2006.01) |
| *G01L 1/22* | (2006.01) |
| *G05G 1/38* | (2008.04) |
| *G05G 1/44* | (2008.04) |
| *G05G 9/04* | (2006.01) |
| *G01L 5/22* | (2006.01) |
| *G01L 5/161* | (2020.01) |
| *A61B 90/00* | (2016.01) |

(Continued)

(52) U.S. Cl.
CPC .............. *A61B 34/25* (2016.02); *A61B 34/30* (2016.02); *A61B 34/74* (2016.02); *G01L 1/044* (2013.01); *G01L 1/22* (2013.01); *G01L 1/2206* (2013.01); *G01L 5/161* (2013.01); *G01L 5/225* (2013.01); *G05G 1/38* (2013.01); *G05G 1/44* (2013.01); *G05G 9/04* (2013.01); *A61B 90/361* (2016.02); *A61B 2017/00973* (2013.01); *A61B 2090/064* (2016.02); *A61F 9/007* (2013.01)

(58) Field of Classification Search
CPC ........ G05G 1/44; G05G 1/445; G06F 3/0334; G06F 3/0383; A63F 13/211; A61B 34/25; A61B 34/30

See application file for complete search history.

(56) References Cited

U.S. PATENT DOCUMENTS

| | | |
|---|---|---|
| 4,970,486 A | 11/1990 | Gray et al. |
| 5,268,624 A | 12/1993 | Zanger |

(Continued)

FOREIGN PATENT DOCUMENTS

| | | |
|---|---|---|
| WO | 9808449 A1 | 3/1998 |
| WO | 2016042407 A1 | 3/2016 |
| WO | 2016179459 A1 | 11/2016 |

OTHER PUBLICATIONS

Define surgical—Google Search, Dec. 27, 2019 (Year: 2019).*

(Continued)

*Primary Examiner* — Vinh Luong

(57) ABSTRACT

A method and system provide a surgical system including a foot pedal and at least one pressure sensor. The foot pedal has a first axis and a second axis. The first axis and the second axis intersect and are oriented at a nonzero angle. The pressure sensor(s) are coupled with the foot pedal. The pressure sensor(s) sense at least one rotation of the foot pedal around the first axis and the second axis. The pressure sensor(s) provide at least one output based on the rotation(s).

8 Claims, 3 Drawing Sheets

(51) Int. Cl.
  *A61B 17/00* (2006.01)
  *A61F 9/007* (2006.01)

(56) References Cited

U.S. PATENT DOCUMENTS

| | | | |
|---|---|---|---|
| 5,554,894 A | 9/1996 | Sepielli | |
| 5,583,407 A | 12/1996 | Yamaguchi | |
| 5,635,777 A | 6/1997 | Telymonde et al. | |
| 5,787,760 A | 8/1998 | Thorlakson | |
| 6,179,829 B1 | 1/2001 | Bisch et al. | |
| 6,225,977 B1 * | 5/2001 | Li | G05G 1/52 345/156 |
| 6,285,356 B1 * | 9/2001 | Armstrong | G05G 9/047 345/167 |
| 6,491,647 B1 * | 12/2002 | Bridger | A61B 5/021 128/900 |
| 6,659,998 B2 | 12/2003 | Dehoogh et al. | |
| 6,862,951 B2 | 3/2005 | Peterson | |
| 6,962,581 B2 | 11/2005 | Thoe | |
| 7,012,203 B2 | 3/2006 | Hanson | |
| 7,019,234 B1 | 3/2006 | Mezhinsky | |
| 7,084,364 B2 | 8/2006 | Mezhinsky | |
| 7,193,169 B2 | 3/2007 | Mezhinsky | |
| 7,381,917 B2 | 6/2008 | Dacquay | |
| 7,619,171 B2 | 11/2009 | Horvath | |
| 8,048,094 B2 | 11/2011 | Finlay | |
| 8,319,125 B2 | 11/2012 | Jo et al. | |
| 8,680,412 B2 | 3/2014 | Horvath | |
| 8,749,188 B2 | 6/2014 | Tran | |
| 9,134,187 B1 | 9/2015 | Organ et al. | |
| 9,240,110 B2 | 1/2016 | Roth | |
| 9,439,806 B2 | 9/2016 | Eastman | |
| 9,795,507 B2 | 10/2017 | Hajishah | |
| 10,195,317 B2 | 2/2019 | Mallough | |
| 10,243,557 B2 | 3/2019 | Ekvall | |
| 10,368,955 B2 * | 8/2019 | Cone | A61B 34/74 |
| 10,503,199 B1 * | 12/2019 | Cone | A61B 17/00 |
| 2003/0214483 A1 | 11/2003 | Hammer et al. | |
| 2006/0145540 A1 | 7/2006 | Mezhinsky | |
| 2006/0156903 A1 | 7/2006 | Baird et al. | |
| 2008/0318679 A1 | 12/2008 | Tran et al. | |
| 2010/0060614 A1 | 3/2010 | Enns | |
| 2010/0198200 A1 | 8/2010 | Horvath | |
| 2013/0038531 A1 * | 2/2013 | Chen | A61F 4/00 345/158 |
| 2014/0035888 A1 * | 2/2014 | Levasseur | G06F 3/0334 345/184 |
| 2014/0267195 A1 | 9/2014 | Enns | |
| 2014/0328469 A1 * | 11/2014 | Lee | A61B 6/44 378/205 |
| 2014/0364864 A1 | 12/2014 | Lynn | |
| 2015/0029047 A1 * | 1/2015 | Levasseur | G05G 9/047 341/21 |
| 2015/0173725 A1 | 6/2015 | Maxson | |
| 2016/0328028 A1 * | 11/2016 | Khojasteh | G06F 3/0334 |
| 2017/0185168 A1 * | 6/2017 | Bonora | G06F 3/011 |
| 2018/0088684 A1 * | 3/2018 | Dillon | G06F 3/0334 |
| 2018/0132958 A1 * | 5/2018 | Jochinsen | A61B 34/74 |
| 2019/0125182 A1 | 5/2019 | Charles | |
| 2019/0163226 A1 * | 5/2019 | Kihara | B60K 26/02 |
| 2019/0350757 A1 | 11/2019 | Charles | |
| 2019/0354200 A1 | 11/2019 | Rapoport | |
| 2019/0354201 A1 | 11/2019 | Rapoport | |
| 2020/0064879 A1 | 2/2020 | Jawidzik | |
| 2020/0085515 A1 | 3/2020 | Jawidzik | |

OTHER PUBLICATIONS

Define surgery—Google Search, Dec. 28, 2019 (Year: 2019).*
Define differential pressure sensor—Google Search, Dec. 28, 2019 (Year: 2019).*
Pressure sensor—Wikipedia, Dec. 28, 2019 (Year: 2019).*
Wootten, et al., "Design and Evaluation of a Multi-Degree-of-Freedom Foot/Pedal Interface for Cycling," International Journal of Sport Biomechanics, 1992, *, 152-164.

* cited by examiner

ERGONOMIC FOOT-OPERATED SYSTEM

This application claims the benefit of priority of U.S. Provisional Patent Application Ser. No. 62/423,272 titled "Ergonomic Foot-Operated Joystick", filed on Nov. 17, 2016, whose inventor is Fred Mercado, which is hereby incorporated by reference in its entirety as though fully and completely set forth herein.

BACKGROUND

During ophthalmic surgery, a surgeon may utilize foot-operated joysticks to manipulate surgical equipment while the surgeon's hands are actively involved in performing the surgery. For example, the surgeon may move the field of view of an imaging system, move a light source or focus a microscope using the foot-operated joystick. The foot-operated joystick may take the form of four push button switches: left, right, up and down. Typically, the surgeon moves his or her foot to depress one of the switches. The surgical device moves in the direction indicated by the switch. For example, an imaging system providing a real-time image on a display may move the field of view shown on the display toward the right of the display in response to the right switch being depressed. If the surgeon depresses the left switch, the field of view may move toward the left on the display. Depressing the up or down switches moves the field of view up and down on the display. As a result, the surgeon can control surgical equipment using their feet.

Although such a foot-operated joystick allows a surgeon to operate equipment without using his hands, the surgeon's hands may not remain stable throughout the process. When moving his foot between the switches, the surgeon frequently moves his leg and upper thigh. This motion results in unwanted movement of the surgeon's hands. Consequently, the surgeon may inadvertently harm the patient's eye. Further, controlling the motion of the surgical instrument based on which switch is depressed may result in the desired location being overshot, undershot or being more difficult to reach.

Accordingly, what is needed is a mechanism for operating surgical equipment independent of and with improved stability for the surgeon's hands.

BRIEF SUMMARY

A method and system provide a surgical system including a foot pedal and at least one pressure sensor. The foot pedal has a first axis and a second axis. The first axis and the second axis intersect and are oriented at a nonzero angle. The pressure sensor(s) are coupled with the foot pedal. The pressure sensor(s) sense at least one rotation of the foot pedal around the first axis and the second axis. The pressure sensor(s) provide at least one output based on the force(s) exerted.

According to the method and system disclosed herein, a user may have improved and simplified control over surgical apparatus that is more independent of the user's hands. Thus, a more ergonomically stable foot-operated joystick may be provided.

DETAILED DESCRIPTION OF THE PREFERRED EMBODIMENTS

Figure 1A:
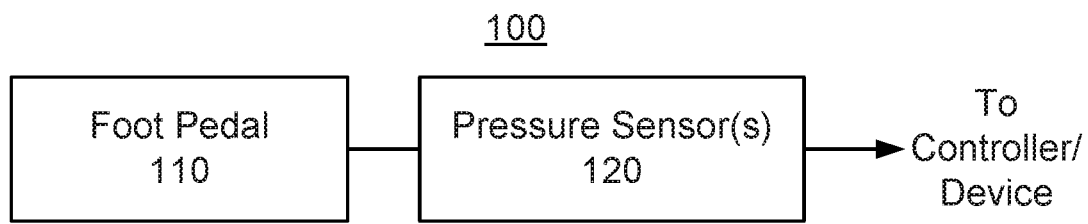
FIG. 1A is a block diagram depicting an exemplary embodiment of a foot controlled surgical system.

The exemplary embodiments relate to surgical systems, (e.g., that may be part of consoles used in ophthalmic surgery). The following description is presented to enable one of ordinary skill in the art to make and use the disclosure and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the disclosure. The exemplary embodiments will also be described in the context of particular methods having certain elements. However, the method and system operate effectively for other methods having different and/or additional elements and elements in different orders that are not inconsistent with the exemplary embodiments. Thus, the present disclosure is not intended to be limited to the embodiments shown, but is to be accorded the widest scope consistent with the principles and features described herein.

In certain embodiments, the system includes one or more processors and a memory. The one or more processors may be configured to execute instructions stored in the memory to cause and control some or all of the process(es) set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system provide a surgical system including a foot pedal and at least one pressure sensor. The foot pedal has a first axis and a second axis. The first axis and the second axis intersect and are oriented at a nonzero angle. The pressure sensor(s) are coupled with the foot pedal. The pressure sensor(s) sense rotation(s) of the foot pedal around the first axis and the second axis. The pressure sensor(s) provide at least one output based on the pressure exerted on the pressure sensor.

Figure 1B:
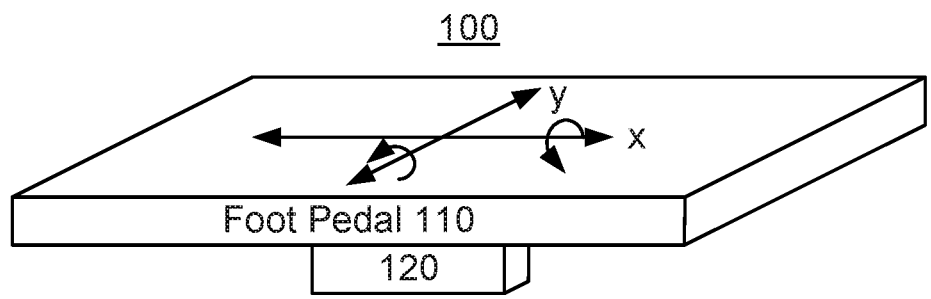
FIG. 1B is a diagram depicting an exemplary embodiment of a foot controlled surgical system.

FIGS. 1A and 1B depict a block diagram and a perspective view of an exemplary embodiment of a foot operated surgical system 100 usable in ophthalmic surgery. FIGS. 1A and 1B are not to scale and for explanatory purposes only. Consequently, some components may be omitted. The surgical system 100 includes a foot pedal 110 and pressure sensor(s) 120. The output of the pressure sensor(s) 120 may be coupled with a controller that is part of the system 100 or coupled to a surgical device controlled by the system 100. Such a surgical device may be considered to be part of or separate from the system 100. The surgical device might include, for example, an optical coherence tomography (OCT) scanner or other imaging system, a microscope, a light source and/or other surgical devices.

The foot pedal 110 has two axes that intersect and are oriented at a nonzero angle. In the embodiment shown, the two axes are the x-axis and the y-axis, which are substantially perpendicular. In other embodiments, the axes may be oriented at another angle. Rotational forces on the foot pedal 110 may be decomposed into a rotation around the x-axis and a rotation around the y-axis. Rotations that are a combination of a rotation around the x-axis and a rotation around the y-axis may thus be made by the foot pedal 110 and sensed by the pressure sensor(s) 120. For example, the foot pedal 110 may be rotated around the x-axis by shifting pressure left to right across the ball on the foot between the Hallux (big toe), and the fifth Phalanges (small toe). The foot pedal 110 may be rotated around the y-axis by applying alternate pressure between the toes and heel. A combination of these motions may rotate the foot pedal 110 around both the x and y axes. Because the foot pedal 110 may rotate around two non-parallel axes, the foot pedal 110 may function as a foot-operated joystick. In some embodiments, the foot pedal 110 may also be rotated around the z-axis, for example by twisting the foot to the right or left. The entire foot pedal 110 might also move downward along a z-axis (not shown) when depressed. Although shown as substantially planar and rectangular, the foot pedal 110 may have another shape. Although shown as adjoining in FIG. 1B, there may be space between the foot pedal 110 and the pressure sensor(s) 120. The foot pedal 110 may thus be free floating at its edges.

The pressure sensor(s) 120 are coupled with the foot pedal 110 such that rotational forces on the foot pedal 110 can be sensed. The pressure sensor(s) 120 sense a pressure or analogous other property corresponding to the rotation(s) of the foot pedal 110. For example, a rotation of the foot pedal 110 around the x-axis results in a positive pressure on one half of the y-axis and a negative pressure on the opposite half of the y-axis. These pressures can be measured to determine the size and direction of rotation of the foot pedal 110 around the x-axis. Such a pressure measurement may be a direct pressure measurement, a strain measurement, a stress measurement or an analogous measurement. As used herein, therefore, a pressure measurement, a strain measurement and/or measurement of another analogous property may be considered pressure measurements. In some embodiments, only the presence of a rotation in a particular direction is measured. In other embodiments, the size of the rotation and/or magnitude of the pressure placed on the foot pedal 110 is measured.

In some embodiments, the pressure sensor(s) 120 directly measure rotation of the foot pedal 110 via pressure. For example, one or more pressure sensor(s) 120 may be located below the foot pedal 110. When the foot pedal 110 is rotated, one or more of the pressure sensor(s) 120 are depressed. The sensor(s) that are depressed depend upon the axis around which the foot pedal 110 is rotated. One of the pressure sensor(s) 120 may be pressed due to a clockwise rotation around the y-axis. Another of the pressure sensor(s) 120 may be pressed due to a counterclockwise rotation around the y-axis. Another pair of the pressure sensor(s) 120 may be used to sense clockwise and counterclockwise rotations around the x-axis. The magnitude of the pressure on each sensor may be also be measured. In some embodiments, a differential measurement of the pressure may be made. The difference in pressure measured by sensors on opposite sides of an axis provides a measure of the rotation of the foot pedal 110. Alternatively, a single sensor which distinguishes between pressure and tension may be used in place of multiple pressure sensors.

In other embodiments, the pressure sensor(s) 120 may indirectly measure the rotation of the foot pedal 110 by measuring properties of other components. For example, the pressure sensor(s) 120 may take the form of strain gauges mounted on one or more leaf springs (not shown in FIGS. 1A-1B) or other component that flexes during rotation of the foot pedal 110. The leaf springs may be physically connected to the foot pedal and allow the foot pedal 110 to be rotated around the x-axis and the y-axis. The strain on a leaf spring depends upon the axis around which the rotation is made, the size of the rotation/pressure on the foot pedal 110 and the direction (clockwise/counterclockwise) of rotation. The strain gauges may be considered to make an indirect measurement of rotations of the foot pedal 110 because the properties of the leaf spring are measured. In either direct or indirect measurements, rotational force(s) around the x and/or y-axes may be sensed via a pressure measurement. In some embodiments, the magnitude of the rotation/pressure applied to rotate the foot pedal 110 as well as the direction of rotation may be sensed using the pressure sensor(s) 120.

In some embodiments, a rotation of the foot pedal 110 around the z-axis (not shown in FIG. 1B) may also be sensed. Such motions may be sensed by the pressure sensor(s) 120 in a manner analogous to that described above for rotations around the x and y axis. A movement of the foot pedal 110 along the z-axis may also be sensed. This may determine the total force exerted by the user on the foot pedal 110.

The pressure sensor(s) 120 sense the rotation of the foot pedal 110 around the x and y axes and provide output(s) based on the rotations. In some embodiments, the output(s) may not only indicate the presence of a rotation, but also the direction and/or size of rotation (or pressure) for one or more of the x-axis, the y-axis and the z-axis. For example, the magnitude(s) of the output(s) (e.g. voltage) of the pressure sensor(s) 120 may be larger for a larger rotation and/or pressure. The sign of the output, the pressure sensor from which the output is provided, the difference between outputs of certain pressure sensors 120, or other combinations of the outputs may indicate the direction of rotation.

The output of the pressure sensor(s) 120 may be used to control a surgical device. For example, the output of the pressure sensor(s) 120 due to a rotation of the foot pedal 110 clockwise/counterclockwise around the x-axis may cause a microscope or OCT scanner to translate or rotate around a first axis to image a different area. As a result, the field of view for the microscope or OCT image moves right or left on a display. The output of the pressure sensor(s) 120 due to a rotation of the foot pedal 110 clockwise/counterclockwise around the y-axis may cause the microscope or OCT scanner to translate in a different direction or rotate around a second axis perpendicular to the first axis. Thus, the field of view for the microscope/OCT image moves up or down on the display. Alternatively, the output of the pressure sensor(s) 120 due to a rotation clockwise/counterclockwise around the y-axis may focus/defocus a microscope. In other embodiments rotation around the z-axis may be used to focus/defocus the microscope, select an area or perform another function. For example, rotation clockwise or counterclockwise around the z-axis might correspond to left clicking or right clicking a mouse. In other embodiments, such rotations may be used to control the area illuminated by a light source. Other surgical devices may be similarly managed. The rotations of the foot pedal 110 around the x-axis, the y-axis and (optionally) the z-axis may be sensed via pressure measurement(s) and an output provided regardless of the purpose(s) of the device controlled or the function(s) corresponding to rotations around specific axes.

The foot-operated surgical system 100 provides a more ergonomically stable mechanism for hands-free control of a surgical device. The foot-operated surgical system 100 may allow a surgeon to control a surgical device simply by rotating the ball of the foot to the left or right (e.g. rotation around the x-axis) or alternately between the ball of the foot and heel (e.g. rotation around the y-axis). The foot pedal 110 may thus be sensitive to smaller pressures made by the surgeon. Because these forces are primarily of the ball and heel of the foot, the surgeon need not move the thigh or use other larger muscle groups that may cause the surgeon's hands to move. Use of the foot-operated surgical system 100 may be better isolated from the surgeon's hands. Consequently, the surgeon's hands may be more stable and less likely to inadvertently injure the patient. The surgeon's ability to operate and patient safety may thus be improved. Rotations that are a combination or rotations of the foot pedal 110 around the x-axis and the y-axis may also be sensed by the pressure sensor(s) 120. The output of the pressure sensor(s) 120 may indicate a directionality corresponding to a combination of these x and y-axis rotations. For example, if an image area is being controlled by the system 100, such an output may allow the image area to move diagonally across the screen, in both the x and y-directions. Consequently, the user need not decompose motions into x direction and y direction motions only. Thus, use of the surgical device being controlled may be improved. Further, the magnitude of the pressure/rotation and direction of the rotation of the foot pedal 110 may be sensed by the pressure sensor(s) 120. The magnitude and direction may thus be part of the output from the pressure sensor(s) 120. As a result, the speed and direction of the change for the surgical device due to input to the foot pedal 110 may be better controlled. For example, a small rotational force around the x-axis may result in a smaller magnitude output from the appropriate pressure sensor(s). The change in the area illuminated by a light source or the field of view may be altered slowly or in smaller increments. Thus, control of the surgical device may be facilitated. Consequently, the foot operated system 100 may improve the surgeon's experience as well as patient safety, particularly for ophthalmic surgery.

Figure 2:
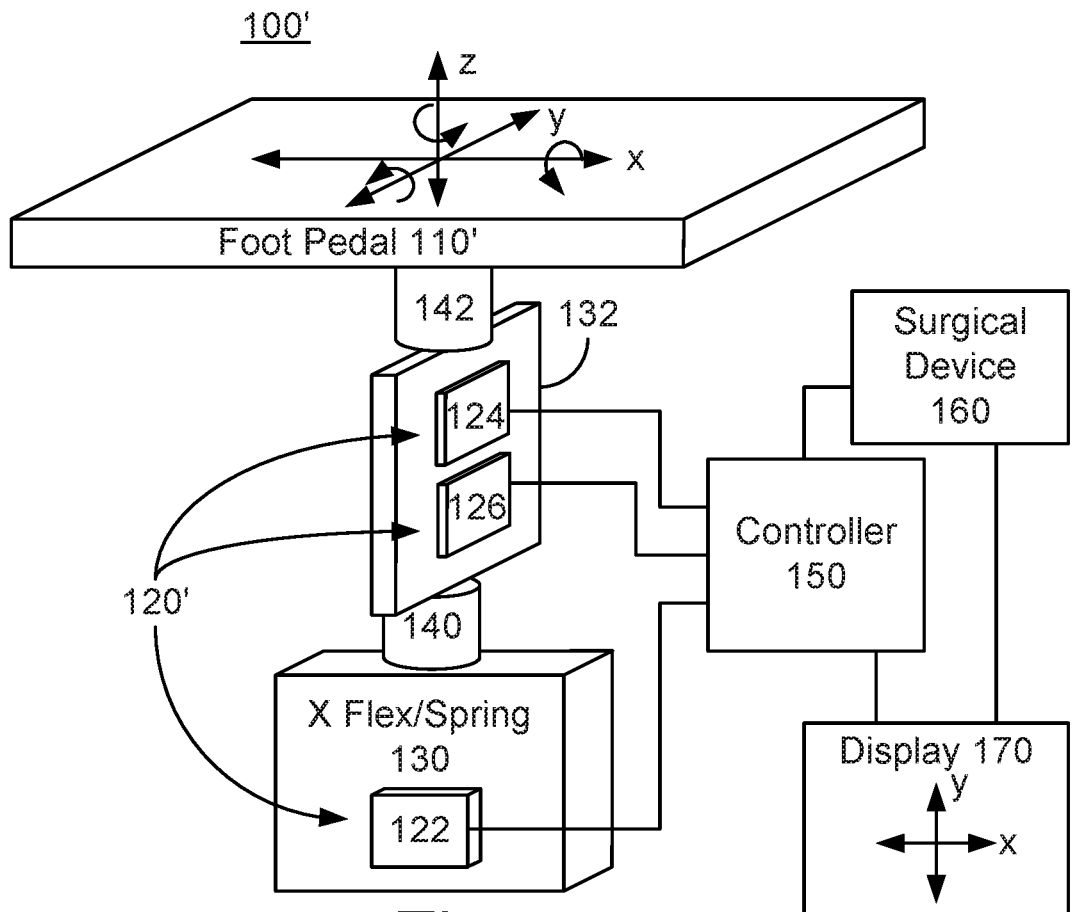
FIG. 2 depicts another exemplary embodiment of a portion of a surgical system that may be controlled by a user's foot.

FIG. 2 depict a diagram depicting another exemplary embodiment of a foot operated surgical system 100' usable in ophthalmic surgery. FIG. 2 not to scale and not all of the components of the system 100' may be shown. The surgical system 100' includes a foot pedal 110' and pressure sensors 120' that are analogous to the foot pedal 110 and pressure sensor(s) 120, respectively. The surgical system 100' also includes couplers 140 and 142 as well as springs 130 and 132. The system 100' also includes sensors 122, 124 and 126 (collectively pressure sensors 120'). Also shown are a controller 150, a surgical device 160 and a display 170. The controller 150 and display 170 may be part of the system 100'. Alternatively, the control 150 and/or display 170 may be part of a separate system that includes the surgical device 160.

The foot pedal 110' includes an x-axis and a y-axis, which are substantially perpendicular and analogous to the axes shown in FIG. 1B. Also shown is the z-axis. Rotations of the foot pedal 110' may be decomposed into rotational force(s) around the x and y-axes. Because the foot pedal 110' may rotate around two non-parallel axes, the foot pedal 110' may function as a foot-operated joystick. The foot pedal 110' may also be spun, or rotated around the z-axis. In alternate embodiments, the entire foot pedal 110''' might also move downward along the z-axis when depressed. This may be sensed and provide an additional mechanism for controlling the surgical device 160. Although shown as substantially planar and rectangular, the foot pedal 110' may have another shape.

The foot pedal 110' is connected to one spring 132 by coupler 142 and then to another spring 130 via coupler 140. The foot pedal 110' may thus be free floating at its edges. In some embodiments, the spring 132 is a spring that flexes along the y-axis (rotations around the x-axis). The spring 130 may thus flex along the x-axis (rotations around the y-axis). In other embodiments, the locations of the springs 130 and 132 may be switched. In alternate embodiments, the springs 130 and/or 132 may be replaced by another number of springs. The spring 130 and/or 132 may be a leaf spring. The springs 130 and 132 may also be oriented substantially perpendicular. Thus, the springs 130 and 132 bend along axes that are perpendicular. This allows the foot pedal 110' to be rotated around both the x-axis and the y-axis. However, in other embodiments, other springs may be used and/or other orientations are possible.

In one embodiments, sensors 122, 124 and 126 are strain gauges coupled with the springs 130 and 132 and used to measure rotations around various axes. When the spring 132 bends along the y-axis, the strain gauge 124 provides an output that is proportional to the force, and thus the pressure, applied to the spring 132. In some embodiments, the sign of the output voltage from the strain gauge 124 indicates the direction the spring 132 has flexed. The sign of the output voltage may indicate the direction of rotation of the foot pedal 110' around the x-axis. Thus, the strain gauge 124 provides an output that indicates the magnitude and direction of rotations around the x-axis. Similarly, when the spring 130 bends along the x-axis, the strain gauge 122 provides an output that is proportional to the force applied to the spring 130. The sign of the output voltage from the strain gauge 122 may indicate the direction the spring 132 has flexed. Thus, the strain gauge 122 provides an output indicating the magnitude and direction of rotations around the y-axis.

The strain gauge 126 is optional. The strain gauge 126 is used to measure rotations around the z-axis by detecting twists in the spring 132. The strain gauge 126 does not provide an output for strains along the length of the spring 132, but does provide a nonzero output based on the difference in strain between the top and bottom of the strain gauge 126 due to twisting of the spring 122. The strain gauge 126 also provides an output proportional to the force exerted around the z-axis. Thus, rotations around the x-axis, the y-axis and the z-axis may be sensed and quantified by the pressure sensors 120'.

The pressure sensors 120' are coupled to and provide their output to controller 150. Although not shown, the controller 150 may include processor(s) that execute program instructions, one or more memories, and other components used in controlling the surgical device 160 and/or the display 170. The controller 150 manages the surgical device 160 and display 170 based upon the outputs of the pressure sensors 120' and, therefore, based upon the input provided by the user via the foot pedal 110'. For example, a rotation around the y-axis sensed by the strain gauge 122 may cause the field of view to move in the positive or negative y direction on the display 170. This change in the field of view is due to motion of the surgical device 160. For example, the controller 150 may provide a control signal to the surgical device 160 that causes the surgical device 160 to undergo translation and/or rotational motion. This control signal is based on the output of the sensor 122. Rotations around the x-axis sensed by the sensor 124 may cause the field of view to move in the positive or negative x direction on the display 170. Rotations around both the x and y axes detected by the sensors 122 and 124 via strain measurements. Such rotational force(s) may result in a diagonal movement of the field of view shown on the display 170 and, therefore, a combination of motions of the surgical device. The speed of movement of the surgical device 160 and, therefore, the field of view on the display may also change based upon the force magnitude measured by the strain gauge(s) 122 and/or 124. Rotations around the z-axis detected by the sensor 126 may have another function. Thus, the surgical device 160 may be controlled via the foot pedal 110'.

Like the system 100, the foot-operated surgical system 100' provides an ergonomic mechanism for hands-free control of a surgical device. A surgeon can control a surgical device simply by rotating the ball of the foot, apply alternate pressure between the toes and heel or twisting the foot. Use of the foot-operated surgical system 100' may better isolate the surgeon's hands. Consequently, the surgeon's ability to operate and patient safety may thus be improved. Rotations that are a combination or rotations of the foot pedal 110' around the x-axis, the y-axis and/or the z-axis may also be sensed by the pressure sensors 120'. The output of the pressure sensors 120' may indicate a directionality corresponding to a combination of these rotations. The magnitude of the pressure/rotation and direction of the rotation of the foot pedal 110' may be sensed by the pressure sensors 120' and used by the controller 150 in managing the surgical device 160. As a result, the speed and direction of the change for the surgical device 160 may be better controlled. Consequently, the foot operated system 100' may improve the surgeon's experience as well as patient safety, particularly for ophthalmic surgery.

Figure 3:
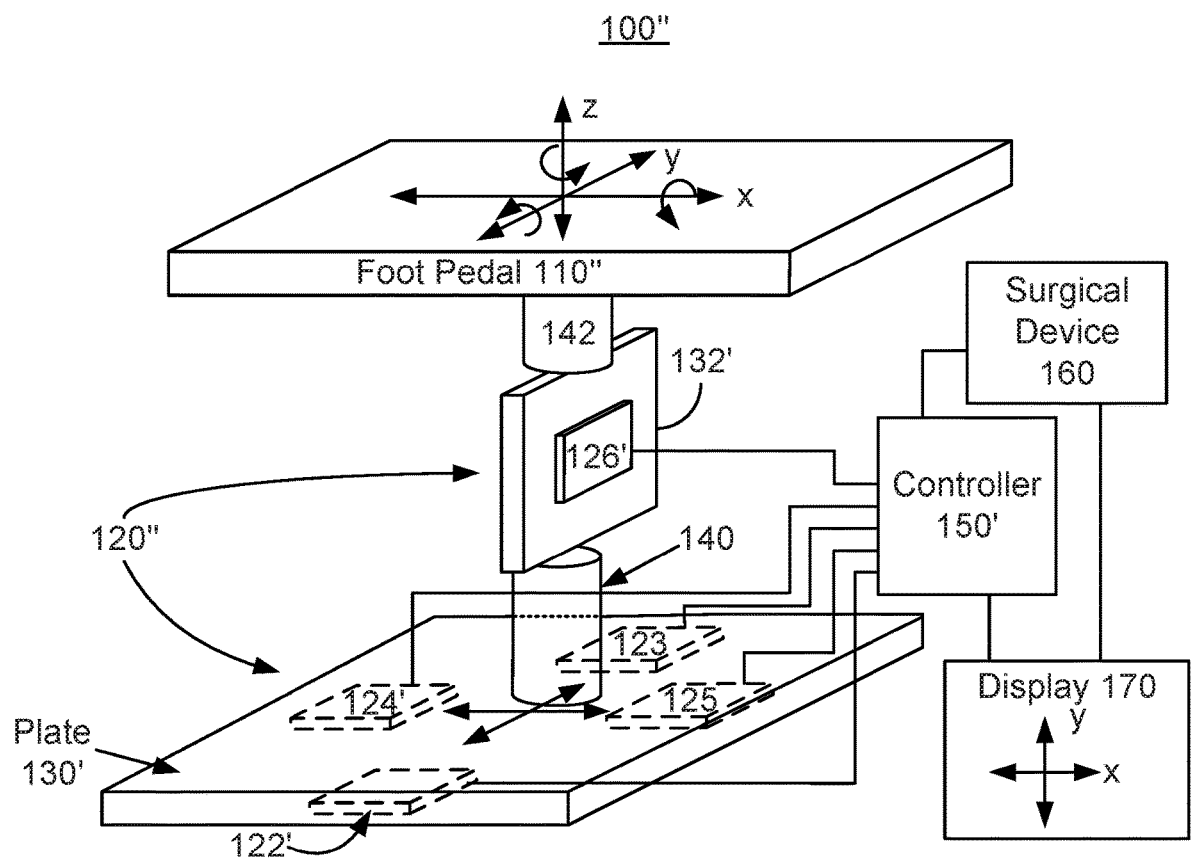
FIG. 3 depicts another exemplary embodiment of a portion of a surgical system that may be controlled by a user's foot.

FIG. 3 depict a diagram depicting another exemplary embodiment of a foot operated surgical system 100" usable in ophthalmic surgery. FIG. 3 is not to scale and not all of the components of the system 100" may be shown. The surgical system 100" includes a foot pedal 110" and pressure sensors 120" that are analogous to the foot pedal 110/110' and pressure sensor(s) 120/120', respectively. The surgical system 100" also includes couplers 140 and 142 as well as plate 130' and spring 132' that are analogous to the couplers 140 and 142 and the springs 130 and 132, respectively. The system 100" includes sensors 122', 123, 124', 125 and 126' (collectively pressure sensors 120") coupled with the plate 130'. While sensors 122', 123, 124', and 125 are shown mounted on the bottom of plate 130', other locations are also contemplated (e.g., on top of plate 130). In another embodiment, the sensors 122', 123', 124' and 125' might be mounted on the foot pedal 110". Also shown are a controller 150, a surgical device 160 and a display 170 analogous to the controller 150, surgical device 160 and display 170 depicted in FIG. 2. The controller 150 and display 170 may be part of the system 100". Alternatively, the control 150 and/or display 170 may be part of a separate system that includes the surgical device 160.

The foot pedal 110" includes an x-axis and a y-axis, which are substantially perpendicular and analogous to the axes shown in FIGS. 1B and 2. Also shown is the z-axis. Rotations of the foot pedal 110" may be decomposed into rotation(s) around the x and y-axes. Because the foot pedal 110" may rotate around two non-parallel axes, the foot pedal 110" may function as a foot-operated joystick. The foot pedal 110" may also be spun, or rotated around the z-axis. In alternate embodiments, the entire foot pedal 110" might also move downward along the z-axis when depressed. This may be sensed and provide an additional mechanism for controlling the surgical device 106. Although shown as substantially planar and rectangular, the foot pedal 110" may have another shape.

The foot pedal 110' is connected to one spring 132' by coupler 142 and then to plate 130' via coupler 140. The foot pedal 110" may thus be free floating at its edges. The spring 132' may have a structure and function analogous to the spring 132. The foot pedal 110" may be rotated around both the x-axis and the y-axis. However, in other embodiments, other springs may be used and/or other orientations are possible.

The pressure sensors 120" are used to measure rotations around various axes. The sensor 126' is analogous to the sensor 126. Thus, the sensor 126' may be used to measure rotations around the z-axis. The pressure sensors 122', 123, 124' and 125 directly measure pressure. For example, the sensors 122', 123, 124' and 125 may be pressure pads. In the embodiment shown, the pressure sensors 120" are located a short distance from the foot pedal 110", which is free floating. In other embodiments, the foot pedal 110" may not be free floating and instead may be in contact with one or more of the pressure sensors 120". The pressure sensors 122' and 123 are located on opposite sides of the x-axis. In the embodiment shown, the pressure sensors 122' and 123 are shown as directly opposite. In other embodiments, the pressure sensors 122' and 123 may be offset. The pressure sensors 122' and 123 measure rotations around the x-axis. The sensor 122' is depressed for a counterclockwise rotation around the x-axis. The sensor 123 is pressed for a clockwise rotation around the x-axis. The magnitude of the pressure applied may also be measured by the pressure sensor 122' and/or the pressure sensor 123. In some embodiments, a differential measurement may be used. For example, the output of the sensor 122' may be subtracted from the output of the sensor 123. This quantity corresponds to the degree of rotation in the clockwise direction around the x-axis. A negative differential measurement is indicative of a counterclockwise rotation.

Similarly, the pressure sensors 124' and 125 are located on opposite sides of the 4-axis. In the embodiment shown, the pressure sensors 124' and 125 are shown as directly opposite. In other embodiments, the pressure sensors 124' and 125 may be offset. The pressure sensors 124' and 125 measure rotations around the y-axis. The sensor 124' is depressed for a counterclockwise rotation around the y-axis. The sensor 125 is pressed for a clockwise rotation around the y-axis. The magnitude of the pressure applied may also be measured by the pressure sensor 124' and/or the pressure sensor 125. In some embodiments, a differential measurement may be used. For example, the output of the pressure sensor 124' may be subtracted from the output of the pressure sensor 125. This quantity corresponds to the degree of rotation in the clockwise direction around the y-axis. A negative differential measurement is indicative of a counterclockwise rotation. Alternatively, a first pressure sensor which distinguishes between pressure and tension may be used in place of pressure sensors 122' and 123 and a second pressure sensor which distinguishes between pressure and tension may be used in place of pressure sensors 124' and 125.

The pressure sensors 120" are coupled and provide their output to controller 150. Although not shown, the controller 150 may include processor(s) that execute program instructions, one or more memories, and other components used in controlling the surgical device 160 and/or the display 170. The controller 150 manages the surgical device 160 and display 170 based upon the outputs of the pressure sensors 120" and, therefore, based upon the input provided by the user via the foot pedal 110'. The controller 150, surgical device 160 and display 170 may function substantially as described above. In this case, however, the controller 150 uses the output of the pressure sensors 122', 123, 124' and 125 and the strain gauge 126' instead of the output of the strain gauges 122, 124 and 126. Thus, the surgical device 160 may be controlled via the foot pedal 110'.

The foot-operated surgical system 100" may share the benefits of the system(s) 100 and/or 100'. A surgeon to control a surgical device simply by rotating the ball of the foot, apply alternate pressure between the toes and heel or twisting the foot. Use of the foot-operated surgical system 100" allow for improved stability of the surgeon's hands. Consequently, the surgeon's ability to operate and patient safety may thus be improved. Rotations that are a combination or rotations of the foot pedal 110" around the x-axis, the y-axis and/or the z-axis may also be sensed by the pressure sensors 120". The output of the pressure sensors 120" may indicate a directionality corresponding to a combination of these rotations. The magnitude of the pressure/rotation and direction of the rotation of the foot pedal 110" may be sensed by the pressure sensors 120" and used by the controller 150 in managing the surgical device 160. As a result, the speed and direction of the change for the surgical device 160 may be better controlled. Consequently, the foot operated system 100" may improve the surgeon's experience as well as patient safety, particularly for ophthalmic surgery.

Figure 4:
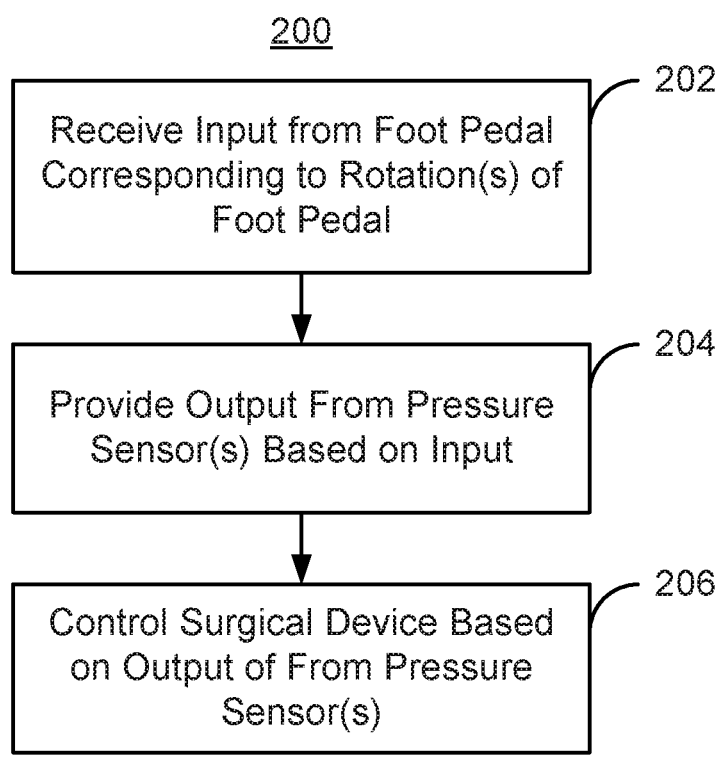
FIG. 4 is a flow chart depicting an exemplary embodiment of a method for treating an ophthalmic condition using a foot operated surgical system.

FIG. 4 is a flow chart depicting an exemplary embodiment of a method 200 for treating an ophthalmic condition using a foot operated surgical system. For simplicity, some elements of the method may be omitted, interleaved, performed in another order and/or combined. The method 200 may include executing instructions on one or more processors. Further, the method 200 is described in the context of ophthalmic surgery using the surgical system 100'. However, the method 200 may be extended to other types of surgery and other analogous foot operated systems such as the system 100 and/or 100".

The method may commence after surgery has started. Thus, the surgeon may have made incision(s) in the eye of the patient, performed other required tasks, and inserted the aspiration and/or irrigation line(s) in the eye of the patient. The surgeon may then wish to accomplish a task using the foot operated surgical system 100'.

The system 100' receives an input from the user, via 202. The input is the user (e.g. a surgeon) depressing the foot pedal 110'. For example, the surgeon may apply alternate pressure using the toes and/or rotate the ball of the foot left or right. As a result, the foot pedal 110' is rotated around the x-axis and/or the y-axis. In some embodiments, the input could include the surgeon twisting the foot to rotate the foot pedal 110' around the z-axis. Because of the configuration of the system 100', this rotation is sensed by one or more of the pressure sensors 120' using pressure measurement(s) or analogous measurement(s) such as strain measurement(s).

Output corresponding to the rotation is provided by the pressure sensors 120', via 204. For example, the pressure sensors 120' may provide an output voltage having a magnitude and sign that depends upon the pressure applied to the foot pedal 110' and the direction the foot pedal 110' rotates around one or more of the axes. This output may be provided to the controller 150.

A surgical device 160 is controlled based on the output of the pressure sensors 120', via 206. For example, the speed and a direction the surgical device 160 is moved or rotated, how fast a magnification is increased or decreased, or other property of the surgical device 160 may be managed based upon the output off the pressure sensors 120'. Thus, the magnitude of the pressure applied to the foot pedal 110' and the direction of rotation of the foot pedal 110' may be used to control the surgical device 160.

Using the method 200 the surgeon may control a surgical device 160 with improved stability of the surgeon's hands. Consequently, the surgeon's ability to operate and patient safety may thus be improved. Further, because of the configuration of the system 100', the motion of the surgical device 160 may be more easily and better controlled. Consequently, the foot operated system 100, 100', 100" and method 200 may improve the surgeon's experience as well as patient safety, for example, in ophthalmic surgery.

The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

I claim:

1. A system comprising:
   a foot pedal having a first axis and a second axis, the first axis and the second axis intersecting and oriented at a nonzero angle;
   at least one pressure sensor coupled with the foot pedal, the at least one pressure sensor for sensing at least one rotation of the foot pedal around the first axis and the second axis and for providing at least one output based on the at least one rotation;
   a first spring corresponding to the first axis;
   a second spring corresponding to the second axis; and
   wherein the at least one pressure sensor includes a first strain gauge and a second strain gauge, the first strain gauge being coupled with the first spring and measuring a first strain on the first spring, the first strain corresponding to a first rotation around the first axis, the second gauge being coupled with the second spring and measuring a second strain on the second spring, the second strain corresponding to a rotation around the second axis.

2. The system of claim 1 wherein the first spring is a first leaf spring and wherein the second spring is a second leaf spring.

3. The system of claim 1 further comprising:
a pivot rotation gauge for measuring a rotation around a third axis, the third axis being substantially perpendicular to the first axis and the second axis.

4. The system of claim 1 wherein the at least one pressure sensor measures at least one pressure magnitude and at least one rotation direction of the at least one rotation around the first axis and the second axis.

5. The system of claim 4 wherein the at least one output indicates the at least one pressure magnitude and the at least one rotation direction.

6. The system of claim 1 wherein the at least one pressure sensor includes at least one differential pressure sensor.

7. A system comprising:
a foot pedal having a first axis and a second axis, the first axis and the second axis intersecting and being substantially perpendicular;
a first spring corresponding to the first axis and coupled to the foot pedal;
a second spring corresponding to the second axis and coupled to the foot pedal;
a plurality of pressure sensors coupled with the foot pedal, the plurality of pressure sensors including a first pressure sensor and a second pressure sensor,
the first pressure sensor for sensing a first pressure difference having a first magnitude, a first direction and corresponding to a first rotation around the first axis,
the second pressure sensor for sensing a second pressure difference having a second magnitude, a second direction and corresponding to a second rotation around the second axis,
the plurality of pressure sensors providing at least one output indicating the first magnitude, the second magnitude, the first direction and the second direction; and
wherein the first pressure sensor is a first strain gauge and the second pressure sensor is a second strain gauge, the system further including:
a pivot rotation gauge for measuring a rotation around a third axis, the third axis being substantially perpendicular to the first axis and the second axis.

8. The system of claim 7 wherein the plurality of pressure sensors include a third pressure sensor and a fourth pressure sensor, the third pressure sensor and the first pressure sensor for sensing the first pressure difference, the fourth pressure sensor and the second pressure for sensing the second pressure difference corresponding to a second rotation around the second axis.

* * * * *